United States Patent [19]

Liu et al.

[11] Patent Number: 5,004,746
[45] Date of Patent: Apr. 2, 1991

[54] ANTI-RETROVIRAL CASTANOSPERMINE ESTERS

[75] Inventors: Paul S. Liu; Sai P. Sunkara, both of Cincinnati; Terry L. Bowlin, Maineville, all of Ohio

[73] Assignee: Merrell Dow Pharmaceuticals Inc., Cincinnati, Ohio

[21] Appl. No.: 102,070

[22] Filed: Sep. 29, 1987

[51] Int. Cl.$^5$ .............................................. A61K 31/44
[52] U.S. Cl. ..................................... 514/299; 546/112
[58] Field of Search ......................... 514/299; 546/112

[56] References Cited

U.S. PATENT DOCUMENTS 4,952,585  8/1990  Sunkara et al. .................... 514/299

FOREIGN PATENT DOCUMENTS

87/03903  7/1987  World Int. Prop. O. .

Primary Examiner—Prince E. Willis
Assistant Examiner—E. McAvoy
Attorney, Agent, or Firm—Stephen L. Nesbitt

[57] ABSTRACT

Certain Castanospermine ester derivatives are disclosed to be effective in treating retroviral infections including HIV infections and are thus useful in the treatment of AIDS and ARC.

28 Claims, No Drawings

ANTI-RETROVIRAL CASTANOSPERMINE ESTERS

This invention relates to the use of certain castanospermine esters in the treatment of retroviral infections including HIV infections.

BACKGROUND OF THE INVENTION

A great deal of research is currently underway to develop treatments and cures for viral infections in humans and in animals. Notably the incidence of AIDS and ARC in humans is increasing at an alarming rate The five year survival rate for those with AIDS is dispiriting and AIDS patients, whose immune systems have been seriously impaired infections including Kaposi's sarcoma and *Pneumocystis carninii* pneumonia. No cure is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromasomal DNA of the host cell making possible viral replication by later translation of the integrated DNA containing the viral genome.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

Retroviruses have, in addition to the usual viral capsid, an outer membrane of lipid and glycoprotein, similar to the membrane of ordinary cells. Indeed the lipid of the retroviral membrane is probably derived directly from the membrane of a previously infected host cell, however, the glycoprotein of the viral membrane is unique to the virus itself and is coded for by the viral genome. Infection of a host cell by a retrovirus initially relies on the interaction of various receptors on the host cell surface with the glycoprotein membrane envelope of the virus. Subsequently the virus and cell membranes fuse and the virion contents are released into the host cell cytoplasm. The glycoprotein envelope of the retroviruses plays an important role in both the initial interaction of the virion and the host cell and in the later fusion of the viral and host cell membranes.

Interference with the formation of the viral envelope glycoprotein could prevent the initial virus-host cell interaction or subsequent fusion or could prevent viral duplication by preventing the construction of the proper glycoprotein required for the completion of the viral membrane. It has been recently reported that the nonspecific glycosylation inhibitors 2-deoxy-D-glucose and β-hydroxy-norvaline inhibit expression of HIV glycoproteins and block the formation of syncytia H. A. Blough, et al., *Biochemical and Biophysical Research Communications*, 141(1), 33-38 (1986). Viral multiplication of HIV-infected cells treated with these agents is stopped, presumably because of the unavailability of glycoprotein required for viral membrane formation. In another report, the glycosylation inhibitor 2-deoxy-2-fluoro-D-mannose was found to exhibit antiviral activity against influenza infected cells by preventing the glycosylation of viral membrane protein. W. McDowell, et al., *Biochemistry*, 24(27), 8145-52 (1985). This report also studied the antiviral activity of 2-deoxyglucose and 2-deoxy-2-fluoroglucose and found that each inhibit viral protein glycosylation by a different mechanism. Many other known glycosylation inhibitors are found to have no antiviral activity. Thus the antiviral activity against membraned viruses, in general, and the anti-retroviral activity, specifically, of glycosylation inhibitors is quite unpredictable.

Castanospermine is an alkaloid which has been isolated from the seeds of *Castanospermum australe* and it has the following formula:

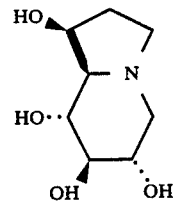

Systematically, this compound can be named in several ways as follows [1S-(1α,6β,7α,8β,8aβ)]-octahydro-1,6,7,8-indolizinetetrol or (1S,6S,7R,8R,8aR)-1,6,7,8-tetrahydroxyindolizidine or 1,2,4,8-tetradeoxy-1,4,8-nitrilo-L-glycero-D-galcto-octitol. The term "castanospermine" or the first systematic name will be used in the discussion below The isolation of this compound and the determination of its structure has been described by L. D. Hohenshutz, et al., *Phytochemistry*, 20, 811 (1981). As part of his study of castanospermine, Hohenshutz obtained castanospermine tetraacetate by the reaction of castanospermine with a very large excess of acetic anhydride but there is no suggestion of any other esters of castanospermine in the article The applicants have now discovered that certain esters of castanospermine are useful in the treatment of various retroviral infections including in the treatment of AIDS and ARC resulting from infection by HIV or other retroviruses.

SUMMARY OF THE INVENTION

The present invention is directed to certain ester derivatives of castanospermine. More particularly, it is directed to compounds having the following formula:

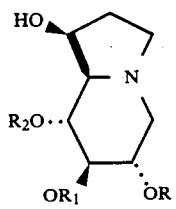

wherein R, $R_1$ and $R_2$ are independently hydrogen, $C_{1-14}$ alkanoyl, cyclohexanecarbonyl, $C_{1-6}$ alkoxyacetyl,

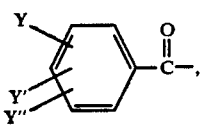

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_{1-10}$ alkyl; thiophenecarbonyl optionally substituted by methyl or halogen; or furancarbonyl optionally substituted by methyl or halogen;

Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy halogen or it is combined with Y to give 3,4-methylenedioxy; Y" is hydrogen, $C_{1-4}$ alkyl, $C_{1-4}$ alkoxy or halogen; with R, $R_1$ and $R_2$ being selected in such a way that at least one of them, but not more than two of them, is hydrogen; or a pharmaceutically acceptable salt of these compounds.

DETAILED DESCRIPTION OF THE INVENTION

The $C_{1-4}$ alkanoyl groups referred to above can be straight- or branched-chain or cyclic and can be exemplified by formyl, acetyl, propionyl, butyryl, isobutyryl, cyclopropanecarbonyl, hexanoyl, octanoyl and decanoyl. The C1-6 alkoxyacetyl referred to above can be methoxyacetyl, ethoxyacetyl and butoxyacetyl. The halogens referred to above can be exemplified by fluorine, chlorine, bromine or iodine. The $C_{2-6}$ alkanoyl groups referred to above can be exemplified by acetyl, propionyl, butyryl, isobutyryl, and hexanoyl. The $C_{1-4}$ alkyl groups referred to above, whether alone or as part of an alkoxy, an alkylsulfonyl or an alkylmercapto group, can be straightor branched-chain alkyl groups containing up to 4 carbon atoms. Examples of various such groups are methyl, ethyl, propyl, butyl, methoxy, ethoxy, butoxy, methylsulfonyl, ethylsulfonyl, methylmercapto and ethylmercapto. The phenyl($C_{2-6}$ alkanoyl) groups referred to above can be exemplified by benzeneacetyl and benzenepropionyl. The various naphthalenecarbonyl, pyridinecarbonyl, thiophenecarbonyl and furancarbonyl groups referred to above include the various position isomers and these can be exemplified by naphthalene-1-carbonyl, naphthalene-2-carbonyl, nicotinoyl, isonicotincyl, N-methyl-dihydropyridine-3-carbonyl, thiophene-2-carbonyl, thiophene-3-carbonyl, furan-2-carbonyl and furan-3-carbonyl. The naphthalene, pyridine, thiophene and furan groups can be optionally further substituted as indicated above.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution In general the acid addition salts of the compounds of this invention are crystalline materials which are soluble in water and various hydrophilic organic solvents and which in comparison to their free base forms, demonstrate higher melting points and an increased solubility.

Preferred compounds of the present invention are those wherein R, $R_1$ and $R_2$ are 1 or 2 alkanoyl or benzoyl groups with the benzoyl substituted by Y, Y' and Y" as described above, especially a $C_{1-4}$ alkanoyl or a benzoyl optionally substituted with an alkyl or halogen. More preferred are those compounds of formula 1 wherein one of R, $R_1$ and $R_2$ is alkanoyl or benzoyl, especially a $C_{1-4}$ alkanoyl or a benzoyl optionally substituted with an alkyl or halogen, and the others are hydrogens. Even more preferred are those compounds of formula 1 wherein one of R, $R_1$ and $R_2$ is a $C_{1-4}$ alkanoyl or a benzoyl optionally substituted with an alkyl or halogen, especially a methyl, bromo, chloro, or fluoro group, and the others are hydrogens. Most preferred are those compounds of formula 1 wherein $R_1$ is a $C_{1-4}$ alkanoyl or benzoyl optionally substituted with an alkyl or halogen, especially a methyl, bromo, chloro, or fluoro group, most especially a methyl, bromo, chloro, or fluoro group at the para position, and wherein R and $R_2$ are each a hydrogen.

The esters of the present invention are prepared by the reaction of castanospermine with an appropriate acid chloride or anhydride in an inert solvent. The halide can be a chloride or bromide and the anhydride includes mixed anhydrides. The relative amount of the acid halide or anhydride used, the relative amount of solvent, the temperature and the reaction time are all controlled so as to minimize the number of hydroxy groups that will be acylated. Thus, only a limited excess of the acid derivative is used, which means up to about a three-fold excess of the acylating agent. Use of a solvent in relatively large amounts, serves to dilute the reactants and hold down the amount of higher acylated products that form. The solvent used is preferably one that will dissolve the reactants used without reacting with them. It is further preferable to carry out the reaction in the presence of a tertiary amine which will react with and remove any acid formed during the course of the reaction. The tertiary amine can be added to the mixture or it can itself be used in excess and serve as the solvent. Pyridine is a preferred solvent in this regard. As indicated above, the time and the temperature are likewise controlled to limit the amount of acylation that takes place. Preferably, the reaction is carried out with cooling in an ice-bath for a period of about 16 hours to give the monoesters with the reaction time extended to a longer period, such as 7 days, if diesters are desired The reaction can actually be carried out at higher temperatures and, in fact, heating can be used as long as the various factors involved are properly controlled. The fact of the matter is, when the reaction is carried out as described, the final reaction mixture will still contain a considerable amount of unreacted castanospermine. This unreacted material can be recovered from the reaction mixture and recycled in subsequent reactions and thus increase the overall amount of castanospermine converted to ester. This recycling is particularly important when the reaction is carried out under conditions which would favor the isolation of monoesters.

The procedures as described above will generally give 6- or 7-monoesters or 6,7- or 6,8-diesters. Other isomers can be obtained by appropriate use of blocking groups. Thus, for example, castanospermine can be reacted with 2-(dibromomethyl)benzoyl chloride to give the 6,7-diester. This diester is then reacted with an appropriate acid halide or anhydride to give the corresponding 8-ester. The two protecting groups are then readily removed by conversion of the two dibromomethyl groups to formyl (using silver perchlorate and 2,4,6-collidine in aqueous acetone) followed by hydrolysis of the formylbenzoic acid ester obtained using morpholine and hydroxide ion. The indicated procedure can be used in a similar way to give diester isomers.

The ability of the castanospermine ester derivatives of this invention to act as anti-retroviral agents can be demonstrated by their ability to inhibit the growth and replication of murine leukemia virus, an oncogenic retrovirus, as determined by an in vitro XC plaque assay. This assay was performed according to the method of Rowe et al. (*Virology*, 1970, 42, 1136–39) as previously described by L. Hsu, et al. (*J. Virological Methods*, 1980, 1, 167–77) and T. L. Bowlin and M. R. Proffitt (*J. Interferon Res.*, 1983, 3(1), 19–31). Mouse SC-1 cells (fibroblast) ($10^5$) were seeded into each well of 6-well cluster plates (Costar #3506) in 4 ml Minimum Essential Medium (MEM) with 10% Fetal Calf Serum (FCS). Following an 18 hour incubation period (37° C.), Moloney murine leukemia virus (MoLV) was applied at a predetermined titer to give optimal (i.e. countable) numbers of virus plaques. Compounds were added 2 hours prior to addition of the virus. Three days later the culture medium was removed, the SC-1 cell monolayers were exposed to UV irradiation (1800 ergs), and rat XC cells ($10^6$) were seeded into each well in 4 ml MEM. Following an additional 3 day incubation (37° C.), these cells were fixed with ethyl alcohol (95%) and stained with 0.3% crystal violet. Plaques were then counted under low magnification. The antiviral activities of various compounds of this invention are tabulated in Table 1.

TABLE 1

INHIBITORY CONCENTRATION OF VARIOUS CASTANOSPERMINE ESTER DERIVATIVES OF FORMULA 1

| R | $R_1$ | $R_2$ | $IC_{50}$ (μg/ml) |
| --- | --- | --- | --- |
| p-F-Bz | p-F-Bz | H | 10.0 |
| Bz | Bz | H | 10.0 |
| H | 2,4-$Cl_2$-Bz | H | 1.0 |
| Butanoyl | H | Butanoyl | 0.5 |
| Butanoyl | H | H | 0.1 |
| H | Bz | H | 1.0 |
| p-F-Bz | H | H | 10 |
| Bz | H | H | 0.1 |
| H | p-Br-Bz | H | 1.0 |
| p-$CH_3$-Bz | H | H | 1.0 |
| H | p-$CH_3$Bz | H | 1.0 |
| p-$CH_3O$-Bz | H | H | 10 |
| Ac | H | H | 10 |
| 2-Furanoyl | H | H | 1.0 |

"Bz" indicates a benzoyl;
"p-F-Bz" indicates a p-fluorobenzoyl;
"2,4-$Cl_2$-Bz" indicates a 2,4-dichlorobenzoyl;
"p-$CH_3O$-Bz" indicates a p-methoxybenzoyl;
and "Ac" indicates an acetyl.

The castanospermine ester derivatives of this invention can be used to treat a number of diseases and conditions known to be caused by retroviruses including those diseases and conditions caused by murine leukemia virus, feline leukemia virus, cytomegalovirus (CMV), avian sarcoma virus, human immunodeficiency virus (HIV), HTLV-I, and HTLV-II. Those experienced in this field are readily aware of the circumstances requiring anti-retroviral therapy. Applicants consider the use of the castanospermine ester derivatives of this invention to treat HIV infections in humans to be of most importance. The term "patient" used herein is taken to mean mammals such as primates, including humans, sheep, horses, cattle, pigs, dogs, cats, rats and mice.

The amount of the castanospermine ester derivative of formula 1 to be administered can vary widely according to the particular dosage unit employed, the period of treatment, the age and sex of the patient treated, the nature and extent of the disorder treated, and the particular castanospermine ester derivative selected. Moreover the castanospermine ester derivative can be used in conjunction with other agents known to be useful in the treatment of retroviral diseases and agents known to be useful to treat the symptoms of and complications associated with diseases and conditions caused by retroviruses. The anti-retrovirally effective amount of a castanospermine ester derivative of formula 1 to be administered will generally range from about 15 mg/kg to 500 mg/kg. A unit dosage may contain from 25 to 500 mg of the castanospermine ester derivative, and can be taken one or more times per day. The castanospermine ester derivative can be administered with a pharmaceutical carrier using conventional dosage unit forms either orally or parenterally.

The preferred route of administration is oral administration. For oral administration the castanospermine ester derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The castanospermine ester derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include catatonic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the castanospermine ester derivative of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

EXAMPLE 1

A slurry of 4.0 g of castanospermine in 140 ml of pyridine was stirred at room temperature for 30 minutes until essentially all of the solids had dissolved. The solution was cooled to 0° C. in an ice/water bath, and a solution of 5.85 ml of benzoyl chloride in 15 ml of pyridine was added dropwise over 15 minutes under nitrogen. After the addition, the reaction was stirred at 8° C. overnight.

The reaction mixture was partitioned between 225 ml methylene chloride and 300 ml water. The organic layer was separated and the aqueous layer extracted with two 225-ml portions of methylene chloride. The combined organic layers were washed successively with 150 ml of 0.5 N hydrochloric acid, saturated sodium carbonate, water and saturated sodium chloride solutions, and then dried over sodium sulfate. Evaporation of solvents under reduced pressure gave 2.9 g of a tan glassy residue.

This material was slurried in chloroform and a white precipitate formed. These solids were isolated to afford 910 mg of a white powder. Thin layer chromatography (85:15, ethyl acetate:methanol) analysis showed the material to be composed of two components (Rf 0.33 and Rf 0.26). The solid mixture was slurried in 45 ml of 4:1 ethyl acetate:methanol and filtered. The residue was dried in vacuo to provide 350 mg of [1S-(1α,6β,7α,8β,-8aβ)]octahydro-1,6,7,8-indolizinetetrol 6-benzoate as a white powdery solid melting at about 233°–236° C., with decomposition. This corresponded to the less polar component of the mixture. NMR (DMSO-$d_6$) δ 1.5–2.2 (m, 5H), 2.9–3.6 (m, 4 H), 4.1 (m, 1H, $C_1$-$\overline{H}$), 4.3 (d, 1H, -O$\overline{H}$) 4.7 (d, 1H, -OH), 4.8 (sextet, 1H, $C_6$-$\overline{H}$), 5.1 (d, 1H, -O$\overline{H}$), 7.6–8.1 (m, 5 $\overline{H}$, aryl). MS (CI-$\overline{CH_4}$) 294 (MH$^+$), 276 (MH$^+$-$H_2O$), 172 (MH$^+$-$PhCO_2H$).

The filtrate from above was condensed and fractionated by preparative thin layer chromatography (silica gel, 80:20, ethyl acetate:methanol) to provide 120 mg of the more polar component, [1S-(1α,6β,7α,8β,8aβ)]-octahydro 1,6,7,8-indolizinetetrol 7-benzoate as a white powdery solid melting at about 200°–202° C. NMR (DMSO-$d_6$+$D_2O$) 1.5–2. 2 (m, 5H), 2.9–3.1 (m, 2H), 3.6–3.8 (m, 2H), 4.1 (m, 1H, $C_1$-$\overline{H}$), 4.8 (t, 1H, $C_7$-$\overline{H}$), 7.4–8.1 (m, 5H, aryl). MS (CI-$\overline{CH_4}$) 294 (MH$^+$), 276 (MH$^+$-$H_2O$), 172 (MH$^+$-$PhCO_2H$). This compound has the following structural formula:

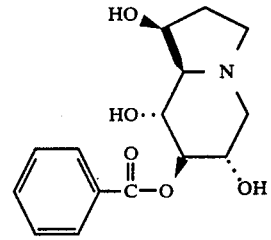

EXAMPLE 2

Castanospermine (1.89 g) was added to a stirred solution of 10 ml of pyridine and cooled to 0° C. in an ice bath. Benzoyl chloride, 3.0 g, was added dropwise to the mixture and the resulting suspension was kept at 0°–4° C. for 7 days. Water, 10 ml, was added and the mixture was evaporated to dryness in vacuo. The resulting residue was redissolved in 1:1 water:ethyl acetate (100 ml) and the phases were separated. The aqueous layer was extracted again with 100 ml of ethyl acetate. The organic extracts were combined and concentrated to a syrup which was shown to be a mixture of two major components by thin layer chromatography (1:1 ethyl acetate:hexane, silica gel, Rf =0.42 and Rf =0.11). The mixture was separated by preparative high pressure liquid chromatography (silica gel, 1:1 ethyl acetate:hexane) to provide 1.9 g (48%) of the more polar [1S-(1α,6β,7α,8β,8aβ)]-octahydro-1,6,7,8-indolizinetetrol 6,7-dibenzoate as a dry foam melting at about 79°-81° C. NMR (DMSO-d$_6$/D$_2$O) δ1.5-2.3 (m, 5H), 3.0-3.4 (m, 2H), 3.9 (t, 1H), 4.2 (m, 1H, C$_1$-H), 5.15 (m, 1H, C$_6$-H), 5.3 (t, 1H, C$_7$-H̄7.4-8.0 (m, 10H̄, aryl). MS (FAB-X̄e) 398 (MH+), 380 (MH+-H$_2$O), 276 (MH+-PhCO$_2$H). The less polar component (Rf =0.42) was isolated as a dry foam melting at about 75°-78° C. which was [1S-(1α,6β,7α,8β,8aβ)]-octahydro-1,6,7,8indolizinetetrol 6,7,8-tribenzoate.

EXAMPLE 3

When the procedure of Example 1 was repeated using castanospermine and the appropriate acid chloride, the following compounds were obtained:
[1S-(1α,6β,7α,8β,8aβ)]-octahydro-1,6,7,8-indolizinetetrol 6-(4-fluorobenzoate) melting at about 216°-218° C.;
[1S-(1α,6β,7α,8β,8aβ)]-octahydro-1,6,7,8-indolizinetetrol 7-(4-fluorobenzoate) melting at about 190°-193° C.;
[1S-(1α,6β,7α,8β,8aβ)]-octahydro-1,6,7,8-indolizinetetrol 7-(2,4-dichlorobenzoate) melting at about 179°-181° C.;
[1S-(1α,6β,7α,8β,8aβ)]-octahydro-1,6,7,8-indolizinetetrol 6-(4-bromobenzoate) melting at about 234°-235° C;
[1S-(1α,6β,7α,8β,8aβ)]-octahydro-1,6,7,8-indolizinetetrol 6-(4-methoxybenzoate) melting at about 221°-224° C.

EXAMPLE 4

When the procedure of Example 2 was repeated using castanospermine and 4-fluorobenzoyl chloride, the product obtained was [1S-(1α,6β,7α,8β,8aβ)]-octahydro-1,6,7,8-indolizinetetrol 6,7-bis(4-fluorobenzoate) melting at about 82°-84° C.

EXAMPLE 5

To a suspension of 3 g of castanospermine in 30 ml of pyridine at 0° C. was added dropwise a solution of 3 g of 4-methylbenzoyl chloride. After the addition, the mixture wad allowed to warm to room temperature and then heated at 55° C. for 24 hours. The reaction mixture was diluted with 10 ml of water and evaporated to dryness in vacuo. The resulting residue was stirred in 150 ml of a 1:2 mixture of water:methylene chloride. The insoluble material was separated by filtration to provide an amorphous off-white solid which was dissolved in 60 ml of hot methanol, treated with 0.5 g of activated charcoal and filtered. The colorless filtrate was cooled to give colorless crystals of [1S-(1α,6β,-7α,8β,8aβ)]-octahydro-1,6,7,8-indolizinetetrol 6-(4-methylbenzoate) melting at about 255°-258° C. with decomposition (580 mg, 12% yield).

The two-phase water/methylene chloride mixture obtained above was evaporated to dryness and the residue was dissolved in 50 ml of a 1:2 mixture of methanol-:ethyl acetate. The solution was fractionated by preparative high pressure liquid chromatography (silica gel, 9:1 ethyl acetate:methanol) and fractions containing the more polar component (i.e., more polar than the 6-ester obtained in the preceding paragraph) were collected and evaporated in vacuo to provide a colorless solid which was [1S-(1α,6β,7α,8β,8aβ)]-octahydro-1,6,7,8-indolizinetetrol 7-(4-methylbenzoate) melting at about 220°-223° C. with decomposition (210 mg, 4% yield).

EXAMPLE 6

When the procedure of Example 5 is repeated using castanospermine and the appropriate acid chloride, the following esters are obtained
6-(3-Methylbenzoate);
7-(3-Methylbenzoate);
6-(3-Trifluoromethylbenzoate);
6-(4-Methylsulfonylbenzoate);
6-(4-Methylmercaptobenzoate);
6-(3-Cyanobenzoate);
6-(4-Dimethylaminobenzoate);
6-(3,4-Methylenedioxybenzoate);
6-(3,4,5-Trichlorobenzoate);
7-(3,4,5-Trichlorobenzoate);
6-(2,4-Dimethylbenzoate);
6-(2-Naphthalenecarboxylate);
7-(2-Naphthalenecarboxylate);
6-(4-Methyl-2-naphthalenecart,oxylate);
6-(Benzeneacetate);
7-(Benzeneacetate);
6-(4-Chlorobenzeneacetate);
6-(Benzenepropionate);
6-(Cinnamate);
7-(Cinnamate);
6-(Cyclohexanecarboxylate);
6-Nicotinoate;
6-Isonicotinoate;
6-(2-Thiophenecarboxylate);
6-(2-Furancarboxylate) melting at about 209-212° C.

EXAMPLE 7

Castanospermine (350 mg) was added to 5 ml of pyridine and stirred under nitrogen at room temperature. Butyric anhydride (0.97 g) was added dropwise and the mixture was kept at room temperature for 24 hours. The reaction mixture was evaporated to dryness in vacuo to leave a syrupy residue. The residue was dissolved in ether and a colorless solid precipitated when pentane was added. Recrystallization of the solid from a mixture of ether and petroleum ether gave colorless needles of [1S-(1α,6β,7α,8β,8aβ)]- octahydro-1,6,7,8-indolizinetetrol 6,8-dibutanoate melting at about 110°-111° C. (22 mg, 4% yield). NMR (CDCl$_3$) δ3.7 (t, 1H, C$_7$-H̄), 4.1 (m, 1H, C$_1$-H), 4.85 (t, 1H, C$_8$-H̄), 5.0 (m, 1H, C$_6$-H̄). MS (CI-CH$_4$) 330 (MH+), 312 (MH̄+-H$_2$O).

EXAMPLE 8

When the procedure of Example 7 is repeated using acetic anhydride, propionic anhydride or caproic anhydride in place of the butyric anhydride, the corresponding 6,8-diesters are obtained.

EXAMPLE 9

To a stirred suspension of 1.5 g of castanospermine in 15 ml of pyridine cooled at 0° C. in an ice-bath was added dropwise 1.0 g of butyryl chloride. The mixture was stirred at room temperature for 3 days and added to a 1:1 mixture of water:methylene chloride (400 ml). After partitioning, the aqueous phase was concentrated in vacuo to provide an oily residue which was fractionated by radial thin layer chromatography (silica gel, 2 mm thickness plate, 2:8 methanol:chloroform) to provide 68 mg of [1S(1α,6β,7α,8β,8aβ)]-octahydro-1,6,7,8indolizinetrol 6-butanoate, homogeneous by thin layer chromatography (silica gel, 2:8 methanol:chloroform, Rf=0.5). Recrystallization of the product from 5:95 isopropanol:hexane gave a colorless solid melting at 113°–114° C. NMR (CDCl$_3$) δ3.5-3.8 (2t, 2H, C$_7$-H and C$_8$-H), 4.4 (m, 1H, C$_1$-H), 4.95 (m, 1H, C$_6$-H). MS (CI-CH$_4$) 260 (MH+), 242 (MH+-H$_2$O), 172 (MH+-C$_3$ Similarly, when the above procedure was repeated using acetyl chloride or propionyl chloride, the following monoesters were obtained:

[1S-(1α,6β,7α,8β,8aβ)]-octahydro-1,6,7,8-indolizinetetrol 6-acetate melting at about 188°–189° C.

[1S-(1α,6β,7α,8β,8aβ)]-octahydro-1,6,7,8-indolizinetetrol 7-propionate melting at about 153°–155° C.

EXAMPLE 10

Tablets are prepared each having the composition:

| | |
|---|---|
| [1S-(1α, 6β, 7α, 8β, 8aβ)]-octahydro-1,6,7,8-indolizinetetrol 6-benzoate | 250 mg |
| starch | 40 mg |
| talc | 10 mg |
| magnesium stearate | 10 mg |

EXAMPLE 11

Capsules are prepared each having the composition:

| | |
|---|---|
| [1S-(1α, 6β, 7α, 8β, 8aβ)]-octahydro-1,6,7,8-indolizinetetrol 6,7-dibenzoate | 400 mg |
| talc | 40 mg |
| sodium carboxymethylcellulose | 40 mg |
| starch | 120 mg |

Injectable dosages forms are prepared each having the composition:

| | |
|---|---|
| [1S-(1α, 6β, 7α, 8β, 8aβ)]-octahydro-1,6,7,8-indolizinetetrol 6-(4-fluorobenzoate) | 0.500 g |
| polyoxyethylene sorbitan monooleate | 2.000 g |
| sodium chloride | 0.128 g |
| water for injection qs ad | 20.000 ml |

What is claimed is:

1. A method of treating a retroviral infection in a patient in need thereof which comprises administering to the patient an anti-retrovirally effective amount of a castanospermine ester of the formula:

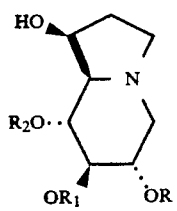

wherein R, R$_1$ and R$_2$ are each independently hydrogen, C$_{1-10}$ alkanoyl, cyclohexanecarbonyl, C$_{1-6}$ alkoxyacetyl,

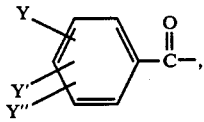

naphthalenecarbonyl optionally substituted by methyl or halogen; phenyl(C$_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by C$_1$-C$_{10}$ alkyl; thiophenecarbonyl optionally substituted by methyl or halogen; or furancarbonyl optionally substituted by methyl or halogen;

Y is hydrogen, C$_{1-4}$ alkyl, C$_{1-4}$ alkoxy, halogen, trifluoromethyl, C$_{1-4}$ alkylsulfonyl, C$_{1-4}$ alkylmercapto, cyano or dimethylamino; Y' is hydrogen C$_{1-4}$ alkyl C$_{1-4}$ alkoxy, halogen or it is combined with Y to give 3,4-methylenedioxy; Y" is hydrogen, C$_{104}$ alkyl, C$_{1-4}$ alkoxy or halogen; with R, R$_1$ and R$_2$ being selected in such a way that at least one of them, but not more than two of them, is hydrogen; or a pharmaceutically acceptable salt thereof.

2. A method of treating a retroviral infection in a patient in need thereof which comprises administering to the patient an anti-retrovirally effective amount of a castanospermine ester of claim 1 wherein R, R$_1$ and R$_2$ are each independently hydrogen, C$_{1-14}$ alkanoyl, C$_{1-6}$ alkoxyacetyl, or

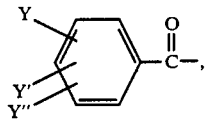

wherein Y is hydrogen, C$_{1-4}$ alkyl, C$_{1-4}$ alkoxy, halogen, trifluoromethyl C$_{1-4}$ alkylsulfonyl, C$_{1-4}$ alkylmercapto, cyano or dimethylamino; Y' is hydrogen, C$_{1-4}$ alkyl, C$_{1-4}$ alkoxy, halogen or it is combined with Y to give 3,4methylenedioxy; Y" is hydrogen, C$_{1-4}$ alkyl, C$_{1-4}$ alkoxy or halogen; with R, R$_1$ and R$_2$ being selected in such a way that at least one of them, but not more than two of them, is hydrogen; or a pharmaceutically acceptable salt thereof 3. A method of treating a retroviral infection in a patient in need thereof which comprises administering to the patient an anti-retrovirally effective amount of a castanospermine ester of claim 1 wherein R, R$_1$ and R$_2$ are each independently hydrogen, C$_{1-4}$ alkanoyl, C$_{1-6}$ alkoxyacetyl, or a benzoyl optionally substituted with an alkyl or halogen; with R, R$_1$ and R$_2$ being selected in such a way that at least one of them, but not more than two of them, is hydrogen; or a pharmaceutically acceptable salt thereof.

4. A method of treating a retroviral infection in a patient in need thereof which comprises administering to the patient an anti-retrovirally effective amount of a castanospermine ester of claim 1 wherein R, R$_1$ and R$_2$ are each independently hydrogen, C$_{1-4}$ alkanoyl, C$_{1-6}$ alkoxyacetyl or a benzoyl optionally substituted with a methyl, bromo, chloro, or fluoro group; with R, R$_1$ and R$_2$ being selected in such a way that at least one of them, but not more than two of them, is hydrogen; or a pharmaceutically acceptable salt thereof.

5. A method of treating a retroviral infection in a patient in need thereof which comprises administering to the patient an anti-retrovirally effective amount of a castanospermine ester of claim 1 wherein $R_1$ is a $C_{1-4}$ alkanoyl, $C_{1-6}$ alkoxyacetyl, or benzoyl optionally substituted with an alkyl or halogen group; or a pharmaceutically acceptable salt thereof.

6. A method of treating a retroviral infection in a patient in need thereof which comprises administering to the patient an anti-retrovirally effective amount of a castanospermine ester of claim 1 wherein $R_1$ is a $C_{1-4}$ alkanoyl, $C_{1-6}$ alkoxyacetyl. Or benzoyl Optionally substituted with a methyl, bromo, chloro, or fluoro group or a pharmaceutically acceptable salt thereof.

7. A method according to claim 1 which is [1S(1α,6β,7α,8β,8aβ)]-octahydro-1,6,7,8-indolizinetetrol 6-benzoate.

8. A method according to claim 1 which is [1S(1α,6β,7α,8β,8aβ)]-octahydro-1,6,7,8-indolizinetetrol 7benzoate.

9. A method according to claim 1 which is [1S-(1α,6β,7α,8β,8aβ)]-octahydro-1,6,7,8-indolizinetetrol 6-(4-methylbenzoate).

10. A method according to claim 1 which is [1S-(1α,6β,7α,8β,8aβ)]-octahydro-1,6,7,8-indolizinete 7-4-bromobenzoate).

11. A method according to claim 1 which is [1S-(1α,6β,7α,8β,8aβ)]-octahydro-1,6,7,8-indolizinetetro 6,8-dibutanoate.

12. A method according to claim 1 which is [1S-(1α,6β,7α,8β,8aβ)]-octahydro-1,6,7,8-indolizinetetr 6-dibutanoate.

13. A method according to claim 1 which is [1S-(1α6β,7α,8β,8aβ)]-octahydro-1,6,7,8-indolizinetetrol 6-(2-furancarboxylate).

14. A method according to claim 1 which is [1S-(1α,6β,7α,8β,8aβ)]-octahydro-1,6,7,8-indolizinetetrol 7-(2,4-dichlorobenzoate).

15. A method of treating a cytomegalovirus infection in a patient in need thereof which comprises administering to the patient an anti-virally effective amount of a castanospermine ester of the formula:

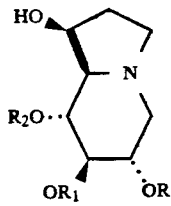

wherein R, $R_1$ and $R_2$ are each independently hydrogen, $C_{1-10}$ alkanoyl, cyclohexanecarbonyl, $C_{1-6}$ alkoxyacetyl,

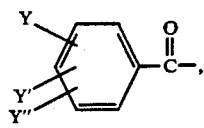

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_{1-10}$ alkyl; thiophenecarbonyl optionally substituted by methyl or halogen; or furancarbonyl optionally substituted by methyl or halogen; Y is hydrogen, $C_{1-4}$ alkyl, $C_{1-4}$ alkoxy, halogen, trifluormethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, $R_1$ and $R_2$ being selected in such a way that at least one of them, but not more than two of them, is hydrogen; or a pharmaceutically acceptable salt thereof.

16. A method of treating a cytomegalovirus patient in need thereof which comprises administering to the patient an antivirally effective amount of a castanospermine ester of claim 15 wherein R, $R_1$ and $R_2$ are each independently hydrogen, $C_{1-14}$ alkanoyl, $C_{1-6}$ alkoxyacetyl, or

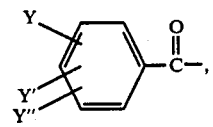

wherein Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, $R_1$ and $R_2$ being selected in such a way that at least one of them, but not more than two of them, is hydrogen; or a pharmaceutically acceptable salt thereof.

17. A method of treating a cytomegalovirus patient in need thereof which comprises administering to the patient an antivirally effective amount of a castanospermine ester of claim 15 wherein R, $R_1$ and $R_2$ are each independently hydrogen, $C_{1-4}$ alkanoyl, $C_{1-6}$ alkoxyacetyl, or a benzoyl optionally substituted with an alkyl or halogen; with R, $R_1$ and $R_2$ being selected in such a way that at least one of them, but not more than two of them, is hydrogen; or a pharmaceutically acceptable salt thereof.

18. A method of treating a cytomegalovirus infection in a patient in need thereof which comprises administering to the patient an anti-virally effective amount of a castanospermine ester of claim 15 wherein R, $R_1$ and $R_2$ are each independently hydrogen, $C_{1-4}$ alkanoyl, $C_{1-6}$ alkoxyacetyl or a benzoyl optionally substituted with a methyl, bromo, chloro, or fluoro group; with R, $R_1$ and $R_2$ being selected in such a way that at least one of them, but not more than two of them is hydrogen; or a pharmaceutically acceptable salt thereof.

19. A method of treating a cytomegalovirus infection in a patient in need thereof which comprises administering to the patient an anti-virally effective amount of a castanospermine ester of claim 15 wherein $R_1$ is a $C_{1-4}$ alkanoyl, $C_{1-6}$ alkoxyacetyl, or benzoyl optionally substituted with an alkyl or halogen group; or a pharmaceutically acceptable salt thereof.

20. A method of treating a cytomegalovirus infection in a patient in need thereof which comprises administering to the patient an anti-virally effective amount of a castanospermine ester of claim 15 wherein $R_1$ is a $C_{1-4}$ alkanoyl, $C_{1-6}$ alkoxyacetyl, or benzoyl optionally substituted with a methyl, bromo, chloro, or fluoro group or a pharmaceutically acceptable salt thereof.

21. A method according to claim 15 which is [1S-1,6α,7α,8β,8aβ)]-octahydro-1,6,7,8-indolizinetetrol 6-benzoate.

22. A method according to claim 15 which is [1S-(1α,6α,7α,8β,8αβ)]-octahydro-1,6,7,8-indolizinetetrol 7-benzoate.

23. A method according to claim 15 which is [1S-(1α,6α,7α,8β,8αβ)]-octahydro-1,6,7,8-indolizinetetrol 6-(4-methylbenzoate)

24. A method according to claim 15 which is [1S-(1α,6α,7α,8β,8αβ)]-octahydro-1,6,7,8-indolizinetetrol 7-(4-bromobenzoate).

25. A method according to claim 15 which is [1S-(1α,6α,7α8β,8αβ)]-octahydro-1,6,7,8-indolizinetrol 6,8-dibutanoate.

26. A method according to claim 15 which is [1S-(1α,6α,7α,8β,8αβ)]-octahydro-1,6,7,8-indolizinetetrol 6-butanoate.

27. A method according to claim 15 which is [1S-(1α,6α,7α,8β,8αβ)]-octahydro-1,6,7,8-indolizinetetrol 6-(2-furancarboxylate).

28. A method according to claim 15 which is [1S-(1α,6α,7α,8β,8αβ)]-octahydro-1,6,7,8-indolizinetetrol 7-(2,4-dichlorobenzoate).

* * * * *

UNITED STATES PATENT AND TRADEMARK OFFICE
CERTIFICATE OF CORRECTION

PATENT NO. : 5,004,746

DATED : April 2, 1991

INVENTOR(S) : Paul S. Liu, Sai Prasad Sunkara, Terry L. Bowlin

It is certified that error appears in the above-identified patent and that said Letters Patent is hereby corrected as shown below:

At column 1, line 16, the patent reads "seriously impaired infections including Kaposi's" and should read --seriously impaired by the infection, suffer from numerous opportunistic infections including Kaposi's--. At column 2, line 32, the patent reads "follows" and should read --follows:--. At column 2, line 34, the patent reads "D-galcto-octitol" and should read --D-galacto-octitol--
      column 2, line 36, the patent reads "below" and should read --below.--. At column 2, line 44, the patent reads "article" and should read --article. At column 3, line 19, the patent reads "alkoxy halogen" and should read --alkoxy, halogen--. At column 3, line 40 the patent reads "straightor" and should read -- straight- or--. At column 3, line 51, the patent reads "isonicotincyl," and should read -- isonicotinoyl,--. At column 4, lines 13-14, the patent reads "solution" and should read --solution.--. At column 4, line 67, the patent reads "desired" and should read --desired.--. At column 5, line 34, the patent reads "Viroloqical" and should read --Virological--. At column 5, line 47, the patent reads "(106)" and should read --(10$^6$)--. At column 7, line 9, the patent reads "acceptably" and should read --acceptable--. At column 7, line 40, the patent reads "catatonic" and should read --cationic--. At column 8, line 18, the patent reads "soluticns," and should read --solutions--. At column 9, line 14, the patent reads "C7-H7.4" and should read -- C$_7$-H), 7.4 --. At column 9, lines 18-19, the patent reads "1,6,7,8in-dolizinetetrol" and should read -- 1,6,7,8-indolizinetetrol". At column 9, line 52, the patent reads "wad" and should read --was--. At column 10, line 13, the patent reads "obtained" and should read --obtained:--.

UNITED STATES PATENT AND TRADEMARK OFFICE
CERTIFICATE OF CORRECTION

PATENT NO. : 5,004,746                                        Page 2 of 3

DATED : April 2, 1991

INVENTOR(S) : Paul S. Liu, Sai Prasad Sunkara, Terry L. Bowlin

It is certified that error appears in the above-identified patent and that said Letters Patent is hereby corrected as shown below:

At column 10, line 27, the patent reads "naphthalenecart,oxylate);" and should read --naphthalenecarboxylate);--. At column 11, line 5, the patent reads "1,6,7,8indolizinetrol" and should read -- 1,6,7,8-indolizinetetrol --. At column 11, line 12, the patent reads "-$C_3$" and should read -- -$C_3H_7CO_2H$). At column 12, line 18, the patent reads "hydrogen $C_{1-4}$" and should read -- hydrogen, $C_{1-4}$ --. At column 12, line 20, the patent reads "$C_{104}$ alkyl" and should read -- $C_{1-4}$ alkyl --
claim 1, line 21. At column 12, line 39, the patent reads "trifluoromethyl $C_{1-4}$" and should read -- trifluoromethyl, $C_{1-4}$ --. At column 12, line 42, the patent reads 3,4methylenedioxy;" and should read --3,4-methylenedioxy;--. At column 13, line 10, the patent reads "alkoxyacetyl. Or benzoyl Optionally" and should read alkoxyacetyl, or benzoyl optionally--. At column 13, line 13, and again at line 15, the patent reads "[1S(1α" and should read -- [1S-(1α, --. At column 13, line 17, that patent reads "7benzoate" and should read -- 7-benzoate --. At column 13, line 22, the patent reads "indolizinete" and should read --indolizinetetrol--. At column 13, line 26, the patent reads "indolizinetetro" and should read --indolizinetetrol--. At column 13, lines 29-30, the patent reads "indolizinetetr 6-dibutanoate." and should read indolizinetetrol  6-butanoate.--.

UNITED STATES PATENT AND TRADEMARK OFFICE
CERTIFICATE OF CORRECTION

PATENT NO. : 5,004,746

DATED : April 2, 1991

INVENTOR(S) : Paul S. Liu, Sai Prasad Sunkara, Terry L. Bowlin

It is certified that error appears in the above-identified patent and that said Letters Patent is hereby corrected as shown below:

At column 13, line 30, the patent reads "(1α6β," and should read -- (1α,6β, --. At column 14, lines 66-67, the patent reads " [1S-1,6α," and should read -- [1S-(1α,6α, --. At column 16, line 2, the patent reads "7α8β," and should read -- 7α,8β, --.

Signed and Sealed this

Twenty-ninth Day of December, 1992

Attest:

DOUGLAS B. COMER

*Attesting Officer*    *Acting Commissioner of Patents and Trademarks*